(12) United States Patent
Schmidt et al.

(10) Patent No.: US 8,362,026 B2
(45) Date of Patent: Jan. 29, 2013

(54) CRYSTALLINE FORM OF 2- CHLORO-5-[3,6-DIHYDRO-3-METHYL-2,6-DIOXO-4-(TRIFLUOROMETHYL)-1-(2H)-PYRIMIDINYL]-4-FLUORO-N-[[METHYL(1-METHYL-ETHYL)AMINO]SULFONYL]BENZAMIDE

(75) Inventors: Thomas Schmidt, Neustadt (DE); Joachim Gebhardt, Wachenheim (DE); Sandra Löhr, Ludwigshafen (DE); Michael Keil, Freinsheim (DE); Jan Hendrik Wevers, Hohen-Sülzen (DE); Peter Erk, Frankenthal (DE); Heidi Emilia Saxell, Ludwigshafen (DE); Gerhard Hamprecht, Weinheim (DE); Werner Seitz, Plankstadt (DE); Guido Mayer, Gönnheim (DE); Bernd Wolf, Fußgönheim (DE); Gerhard Cox, Bad Dürkheim (DE); Alfred Michel, Ramsen (DE); Cyrill Zagar, Hong Kong (CN); Robert Reinhard, Limburgerhof (DE); Bernd Sievernich, Haßloch (DE)

(73) Assignee: BASF SE, Ludwigshafen (DE)

( * ) Notice: Subject to any disclaimer, the term of this patent is extended or adjusted under 35 U.S.C. 154(b) by 411 days.

(21) Appl. No.: 12/444,653

(22) PCT Filed: Oct. 12, 2007

(86) PCT No.: PCT/EP2007/060879
§ 371 (c)(1),
(2), (4) Date: Apr. 7, 2009

(87) PCT Pub. No.: WO2008/043835
PCT Pub. Date: Apr. 17, 2008

(65) Prior Publication Data
US 2010/0105562 A1    Apr. 29, 2010

(30) Foreign Application Priority Data
Oct. 13, 2006    (EP) .................... 06122265

(51) Int. Cl.
*A01N 43/54* (2006.01)
*A61K 31/505* (2006.01)
(52) U.S. Cl. ........................ 514/274; 544/312
(58) Field of Classification Search .............. 544/311, 544/312
See application file for complete search history.

(56) References Cited

U.S. PATENT DOCUMENTS

| 4,885,027 | A | 12/1989 | Pomidor | |
| 7,232,926 | B2 * | 6/2007 | Hamprecht et al. | 562/822 |
| 2004/0249164 | A1 | 12/2004 | Bratz et al. | |
| 2005/0159622 | A1 | 7/2005 | Hamprecht et al. | |
| 2006/0293520 | A1 * | 12/2006 | Hamprecht et al. | 544/309 |
| 2008/0033174 | A1 | 2/2008 | Lohr et al. | |
| 2008/0293941 | A1 | 11/2008 | Gebhardt et al. | |
| 2010/0035905 | A1 * | 2/2010 | Schmidt et al. | 514/274 |

FOREIGN PATENT DOCUMENTS

| WO | WO 01/83459 | 11/2001 |
| WO | WO 0183459 A2 * | 11/2001 |
| WO | WO 03/097589 | 11/2003 |
| WO | WO 2005/054208 | 6/2005 |
| WO | WO 2006/010474 | 2/2006 |
| WO | WO 2006/125746 | 11/2006 |
| WO | WO 2008/043836 | 4/2008 |

OTHER PUBLICATIONS

S.L. Morissette et al., Advanced Drug Delivery Reviews, 56, 275-300 (2004).*
S.R. Vippagunta et al., Advanced Drug Delivery Reviews, 48, 3-26 (2001).*
J.K. Guillory, Generation of Polymorphs, Hydrates, Solvates, and Amorphous Solids, in Polymorphism in Pharmaceutical Solids 183-220 (H.G. Brittain ed., 1999).*
International Search Report completed Apr. 29, 2008, in International Application No. PCT/EP2007/060879, filed Oct. 12, 2007.
English language translation of the International Preliminary Report on Patentability, from corresponding International Application No. PCT/EP2007/060879, filed Oct. 12, 2007.
Khankari et al., "Pharmaceutical hydrates", Thermochimica Acta, vol. 248, 1995, pp. 61-79.
Byrn et al., "Hydrates and Solvates", Solid-State Chemistry of Drugs, 2nd Edition, 1999, pp. 233-247.
Office Action dated Aug. 31, 2011, from U.S. Appl. No. 12/444,651, filed Apr. 7, 2009.

* cited by examiner

*Primary Examiner* — James O Wilson
*Assistant Examiner* — Alexander R Pagano
(74) *Attorney, Agent, or Firm* — Brinks Hofer Gilson & Lione

(57) ABSTRACT

The present invention relates to a crystalline form of 2-chloro-5-[3,6-dihydro-3-methyl-2,6-dioxo-4-(trifluoromethyl)-1-(2H)pyrimidinyl]-4-fluoro-N-[[methyl(1-methylethyl)-amino]sulfonyl]benzamide. The invention also relates to a process for the preparation of this crystalline form and to plant protection formulations which comprise this crystalline form of the phenyluracil.

14 Claims, 2 Drawing Sheets

Figure 1:
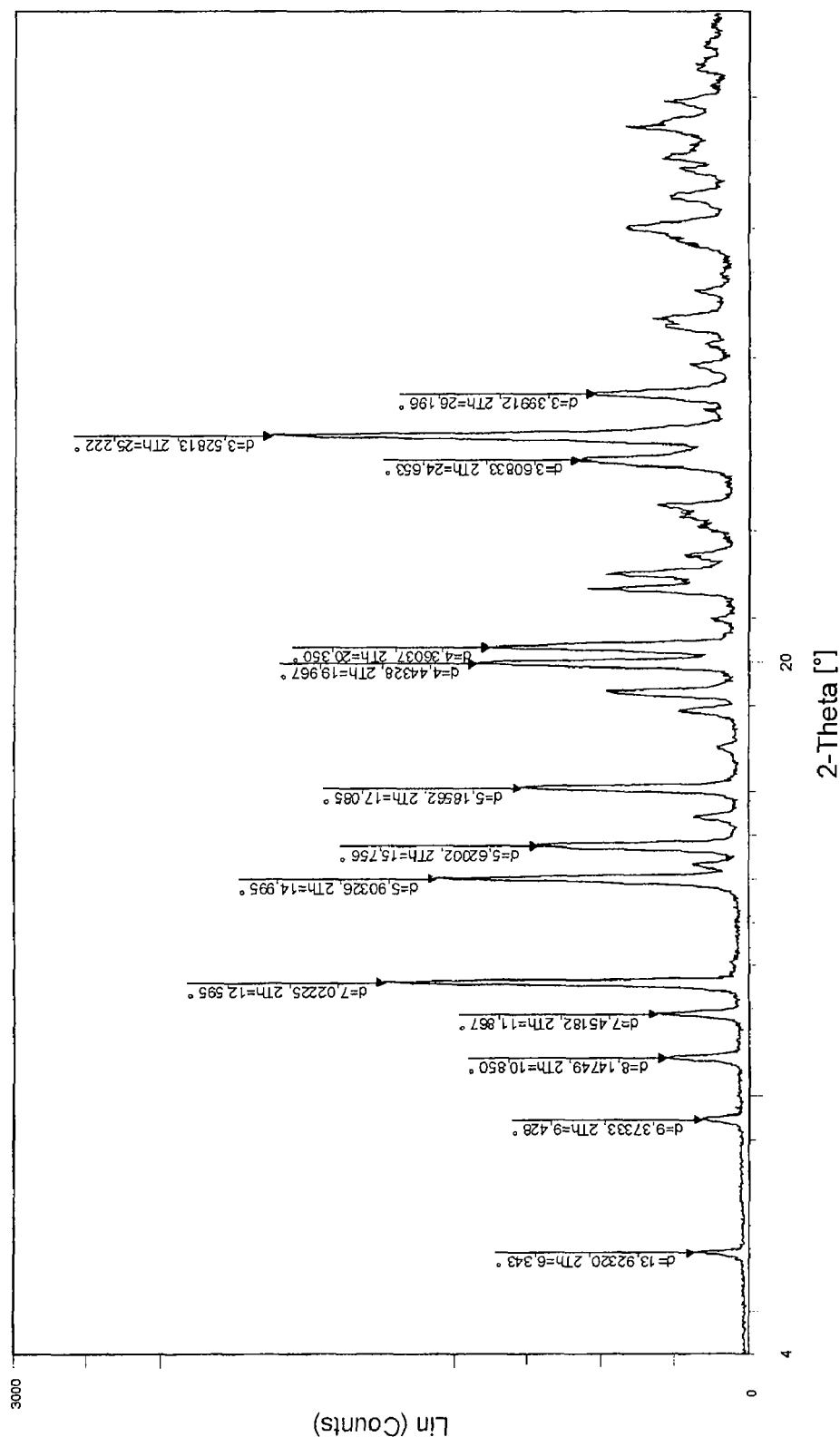

CRYSTALLINE FORM OF 2-CHLORO-5-[3,6-DIHYDRO-3-METHYL-2,6-DIOXO-4-(TRIFLUOROMETHYL)-1-(2H)-PYRIMIDINYL]-4-FLUORO-N-[[METHYL(1-METHYL-ETHYL)AMINO]SULFONYL] BENZAMIDE

This application is a National Stage application of International Application No. PCT/EP2007/060879, filed Oct. 12, 2007. This application also claims the benefit under 35 U.S.C. §119 of European Patent Application No. 06122265.9, filed Oct. 13, 2006.

The present invention relates to a crystalline form of 2-chloro-5-[3,6-dihydro-3-methyl-2,6-dioxo-4-(trifluoromethyl)-1-(2H)pyrimidinyl]-4-fluoro-N-[[methyl(1-methylethyl)-amino]sulfonyl]benzamide, hereinbelow also referred to as phenyluracil I. The invention also relates to a process for the preparation of this crystalline form and to crop protection formulations which comprise this crystalline form of the phenyluracil.

The phenyluracil I, which has the following formula:

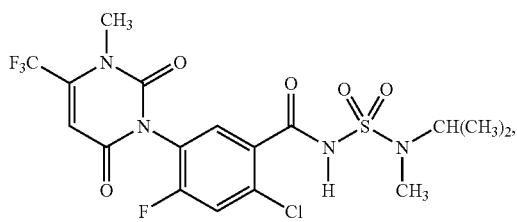

I is a herbicidal active substance which is disclosed in WO 01/083459. Further processes for its preparation are disclosed in WO 03/097589, WO 05/054208 and WO 06/097589 and the earlier international application PCT/EP 2006/062414. All known processes for preparing phenyluracil I provide it as an amorphous substance.

Studies undertaken by the assignee company have demonstrated that the amorphous phenyluracil I is only moderately suitable for the preparation of formulations which comprise the substance as solid. Stability problems may occur in particular in the case of multi-phase formulations.

Surprisingly, it has now been found that suitable processes give a crystalline, essentially solvent-free form of the phenyluracil I which does not have these disadvantages. Moreover, it has, surprisingly, emerged that this crystalline form has a better herbicidal activity and, in a series of crops, has better crop plant tolerance, than the amorphous form of the phenyluracil I known to date. The inventive crystalline form is also more compact than the amorphous form to date and, upon its preparation, is generated in the form of discrete crystals or crystallites. It can therefore be handled with greater ease than form I.

Accordingly, the present invention relates to an essentially solvent-free crystalline form of 2-chloro-5-[3,6-dihydro-3-methyl-2,6-dioxo-4-(trifluoromethyl)-1-(2H)-pyrimidinyl]-4-fluoro-N-[[methyl(1-methylethyl)amino]sulfonyl]benzamide.

To distinguish the inventive, essentially solvent-free, form of the phenyluracil I from the known amorphous form, hereinbelow referred to as form I, the former is hereinbelow also referred to as form II.

Referring to form II, the term "essentially solvent-free" means that the inventive form II comprises no detectable amounts of solvents incorporated into the crystal lattice, i.e. the amount of solvent in the crystal lattice is less than 10 mol %, in particular not more than 5 mol %, based on the phenyluracil I.

The inventive form II can be identified by means of X-ray powder diffractometry on the basis of its diffraction diagram. Thus, an X-ray powder diffractogram recorded at 25° C. using Cu—$K_\alpha$ radiation (1.54178 Å) shows at least 2, as a rule at least 4, frequently at least 6, in particular at least 8 and specifically all of the reflexes detailed in Table 1 hereinbelow as 2θ values, or as interplanar spacings d:

TABLE 1

| 2θ | d [Å] |
|---|---|
| 6.3 ± 0.2° | 14.92 ± 0.3 |
| 9.4 ± 0.2° | 9.37 ± 0.2 |
| 10.9 ± 0.2° | 8.15 ± 0.1 |
| 11.9 ± 0.2° | 7.45 ± 0.05 |
| 12.6 ± 0.2° | 7.02 ± 0.05 |
| 15.0 ± 0.2° | 5.90 ± 0.05 |
| 15.8 ± 0.2° | 5.62 ± 0.04 |
| 17.1 ± 0.2° | 5.19 ± 0.03 |
| 20.0 ± 0.2° | 4.44 ± 0.02 |
| 20.4 ± 0.2° | 4.36 ± 0.02 |
| 24.7 ± 0.2° | 3.61 ± 0.02 |
| 25.2 ± 0.2° | 3.53 ± 0.02 |
| 26.2 ± 0.2° | 3.40 ± 0.02 |

Studies on monocrystals of form II at −170° C. demonstrate that the underlying crystal structure is monoclinic. The unit cell has the space group P2(1)/c. The characteristic data of the crystal structure of form II are compiled in Table 2.

TABLE 2

| Crystallographic characteristics of form II (measured at -170° C.) | |
|---|---|
| Parameter | Form II |
| Class | monoclinic |
| space group | P2(1)/c |
| a | 9.377(5) Å |
| b | 7.698(4) Å |
| c | 28.12(2) Å |
| α | 90° |
| β | 96.37(3)° |
| γ | 90° |
| volume | 2017.1(17) Å 3 |
| Z | 4 |
| Density (calculated) | 1.649 Mg/m3 |
| R1; wR2 | 0.057; 0.149 |
| wavelength | 1.54178 Å | a, b, c = unit cell length
α, β, γ = unit cell angle
Z = number of molecules in the unit cell Besides X-ray powder diffractometry and the crystallographic analysis, differential scanning calorimetry (DSC) may also be employed for identifying form II.

Form II shows a thermogram with a characteristic melting peak in the range between 170 and 200° C. The peak maximum is typically in the range of approximately 180° C. to 190° C. The melting points indicated herein refer to data determined by means of differential scanning calorimetry (DSC, crucible material aluminum, heating rate 5 K/min).

The inventive form II of the phenyluracil I is prepared successfully by controlled crystallization from a solution of the phenyluracil I in an organic solvent which is essentially free from water.

To this end, a solution of the phenyluracil I is provided, in a first step i), in an organic solvent which is essentially free from water, and then, in a second step, a controlled crystallization of the phenyluracil I is brought about.

In this context, essentially free from water means that the concentration of water in the solution comprising the phenyluracil I does not exceed 10% by weight, frequently 5% by weight and in particular 1% by weight, based on the total amount of solvent.

The term "controlled crystallization" is understood as meaning that the crystallization is performed over a prolonged period which, as a rule, amounts to at least 1 h, frequently at least 2 h and in particular at least 3 h. The crystallization may also take place over a prolonged period of up to several days, for example 1, 2 to 3 days. Frequently, however, the crystallization time will not exceed 15 h. Accordingly, the crystallization is, as a rule, carried out over a period of from 1 to 24 h, frequently 2 h to 15 h, in particular 3 to 10 h.

Suitable solvents are, in principle, those organic solvents and solvent mixtures in which the phenyluracil I is sufficiently soluble at elevated temperature, for example has a solubility of at least 100 g/l at 50° C.

Preferred are, furthermore, solvents and solvent mixtures whose boiling point at atmospheric pressure is in the range of from 50 to 160° C.

Examples of suitable solvents are, in particular, the organic solvents detailed hereinbelow, also referred to as solvents L1 hereinbelow:

$C_1$-$C_6$-alkanols such as methanol, ethanol, propanol, n-butanol, isobutanol, tert-butanol, 1-pentanol or hexanol,
acyclic ketones having 3 to 8 carbon atoms such as acetone, methyl ethyl ketone or 3-methylbutan-2-one (isopropyl methyl ketone),
cyclic ketones having 5 to 8 carbon atoms such as cyclohexanone or cycloheptanone,
aromatic hydrocarbons and hydrocarbon mixtures, and aromatic chlorohydrocarbons, in particular mono- and di-$C_1$-$C_3$-alkylbenzenes such as toluene, xylenes, chlorobenzene and dichlorobenzenes,
di-$C_1$-$C_6$-alkyl ethers such as diethyl ether, diisopropyl ether and methyl tert-butyl ether,
5- or 6-membered alicyclic ethers such as tetrahydrofuran (THF) or dioxane,
nitroalkanes having 1 to 3 carbon atoms such as nitromethane,
alkylnitriles having 2 to 6 carbon atoms such as acetonitrile, propionitrile, isobutyronitrile and butyronitrile,
$C_1$-$C_4$-alkyl esters of aliphatic $C_1$-$C_4$-carboxylic acids, in particular $C_1$-$C_4$-alkyl esters of acetic acid, such as ethyl acetate and butyl acetate,
N,N-dimethylamides of aliphatic $C_1$-$C_4$-carboxylic acids such as dimethyl-formamide and dimethylacetamide, and
mixtures of the above solvents.
Preferred organic solvents L1 are
$C_2$-$C_4$-alkanols such as methanol, ethanol, propanol, n-butanol, isobutanol and tert-butanol,
acyclic ketones having 3 to 6 carbon atoms such as acetone, methyl ethyl
ketone or 3-methylbutan-2-one (isopropyl methyl ketone),
mono-$C_1$-$C_3$-alkylbenzenes such as toluene,
di-$C_1$-$C_6$-alkyl ethers such as diethyl ether, diisopropyl ether and methyl tert-butyl ether,
$C_1$-$C_4$-alkyl esters of acetic acid, such as ethyl acetate and butyl acetate,
5- or 6-membered alicyclic ethers such as tetrahydrofuran (THF), and
mixtures of the above solvents.

Especially preferred organic solvents L1 are mono-$C_1$-$C_3$-alkylbenzenes, specifically toluene, and mixtures of mono-$C_1$-$C_3$-alkylbenzenes, specifically of toluene, with tetrahydrofuran. Also preferred are mixtures of the preferred solvents L1, in particular mixtures of mono-$C_1$-$C_3$-alkylbenzenes, specifically mixtures of toluene, with methanol, where even small amounts of methanol (for example up to 20% by volume, in particular up to 10% by volume) lead to an improved purity of the crystallizate obtained.

Also suitable in principle are mixtures of the abovementioned organic solvents L1 with other solvents L2, where the solvent L1 typically accounts for the majority, in particular at least 70% by weight and specifically at least 90% by weight of the solvent employed for the crystallization. In particular, the solvent L1 is the sole solvent, or comprises less than 5% by weight based on the total solvent quantity of an organic solvent other than L1.

The other organic solvents L2 are, in particular,
carbonates having preferably 2 to 6 carbon atoms such as dimethyl carbonate, diethyl carbonate or ethylene carbonate,
$C_1$-$C_6$-alkyl esters of aliphatic $C_1$-$C_4$-carboxylic acids such as methyl acetate, ethyl acetate, propyl acetate, methyl isobutyrate and isobutyl acetate,
hydroxy-$C_1$-$C_4$-alkylaromatics and $C_1$-$C_4$-alkylcarbonylaromatics such as benzyl alcohol and acetophenone,
aliphatic chlorohydrocarbons such as dichloromethane and dichloroethane,
sulfoxides having preferably 2 to 6 carbon atoms such as dimethyl sulfoxide,
sulfones having preferably 2 to 6 carbon atoms such as dimethyl sulfone and tetramethylene sulfone, and
aliphatic and cycloaliphatic hydrocarbons having, as a rule, 5 to 10 carbon atoms, such as hexane, cyclohexane, petroleum ether and petroleum benzine.

The concentration of phenyluracil I in the solution employed for the crystallization will naturally depend on the type of the solvent and the solution temperature and is frequently in the range of from 50 to 800 g/l. Suitable conditions can be determined by the skilled worker on the basis of routine experiments.

Preferably, the phenyluracil I solution employed for the crystallization comprises the phenyluracil I in a purity of at least 85%, frequently at least 90%, in particular at least 95%, i.e. the quantity of organic impurities which are not organic solvent amounts to no more than 15% by weight, frequently no more than 10% by weight and in particular no more than 5% by weight, based on the phenyluracil I which is present in dissolved form in the solvent.

The solution comprising the phenyluracil I can be provided for example by the following methods:

(1) dissolving the phenyluracil I, preferably in a form which differs from form II, in an organic solvent which is essentially free from water; or
(2) preparation of the phenyluracil I by chemical reaction and transfer of the reaction mixture, if appropriate after removal of reagents and/or by-products, into an organic solvent which is suitable in accordance with the invention and is essentially free from water.

In principle, any known form of the phenyluracil I may be employed for preparing the solution by dissolving the phenyluracil I. Naturally, a form of the phenyluracil I which differs from form II will be used. Suitable for this purpose are in particular a solid or liquid melt of the phenyluracil or amorphous phenyluracil I as known from the prior art. Suitable forms of the phenyluracil, other than form I, are also solvates, in particular hydrates, of the phenyluracil I, or a methanol solvate of the phenyluracil I. Also suitable are mixtures of different forms of the phenyluracil. The hydrates of the phenyluracil I are the subject matter of a parallel patent application which is referred to herewith in its entirety.

The solvent used for dissolving the phenyluracil I typically takes the form of one of the abovementioned organic solvents L1 or a mixture of different solvents L1 or a solvent mixture, which comprises at least 70% by weight and specifically at least 90% by weight of solvent L1, based on the total amount of the solvent employed for the purpose of dissolving.

To dissolve the form of the phenyluracil I which differs from form II, the phenyluracil I will usually be incorporated into the solvent in the form of finely particulate solid or as a melt by commixing, which process is carried out at a temperature at which the solvent, or solvent mixture, is capable of fully dissolving the phenyluracil I.

Dissolving the amorphous form I is usually performed at temperatures in the range of from 20 to 160° C. In a preferred embodiment of the invention, dissolving of the phenyluracil I takes place at elevated temperature, in particular at least 50° C., specifically at least 80° C., where, naturally, the temperature employed for dissolving will not exceed the boiling point of the solvent. Frequently, the dissolving is carried out at temperatures in the range of from 50 to 140° C., in particular in the range of from 80 to 120° C. and especially preferably in the range of from 95 to 115° C.

The amount of phenyluracil I which is dissolved in the solvent will naturally depend on the nature of the solvent L1 and the dissolving temperature, and is frequently in the range of from 100 to 800 g/l. Suitable conditions can be determined by the skilled worker by routine experiments.

The solution of the phenyluracil I can also be provided by transferring a reaction mixture which has been obtained as the result of a chemical reaction and which comprises the phenyluracil I into an organic solvent which is essentially free from water and is suitable in accordance with the invention, if appropriate after having removed reagents and/or by-products. Here, a procedure may be followed in which the reaction is carried out in an organic solvent or solvent mixture which is composed at least in part, preferably to at least 50% by weight, of a solvent which is suitable for the crystallization and, if appropriate, a work-up is performed, where excess reagents and any catalysts which may be present and any unsuitable solvent which may be present, e.g. water and/or methanol, are removed. The preparation of a solution of the phenyluracil I by chemical reaction of a suitable precursor of the phenyluracil I, can be performed in analogy to the methods which are described in the prior art cited at the outset, which is herewith referred to in its entirety.

In the event that solvates of the phenyluracil I are employed for preparing the solution, it may be advantageous to remove the solvate solvent after the dissolving step, but before the crystallization step, for example by means of distillation.

The crystallization of form II of the phenyluracil I can be brought about in the customary manner, for example
  by cooling the solution which comprises the phenyluracil I in dissolved form,
  by addition, to the solution which comprises the phenyluracil I in dissolved form, of an organic solvent which reduces the solubility, in particular by addition of an anhydrous nonpolar organic solvent;
  by concentrating the solution which comprises the phenyluracil I in dissolved form, or
  by a combination of the abovementioned measures.

As a rule, the crystallization is performed to such an extent that at least 80% by weight, preferably at least 90% by weight, of the phenyluracil I employed crystallize out.

In a preferred embodiment of the invention, a procedure will be followed in which the solution which comprises the phenyluracil I in dissolved form is prepared at elevated temperature, preferably at least 50° C., for example 50 to 150° C., preferably 80 to 120° C. and especially preferably in the range of from 100 to 115° C., and the crystallization of the phenyluracil I is subsequently brought about by cooling and, if appropriate, concentrating the solution. Preferably, the solution of the phenyluracil I will be cooled by at least 20 K, in particular by 30 to 60 K, in order to initiate the crystallization. The cooling procedure can be performed in a controlled fashion, i.e. at a slow cooling rate of, as a rule, not more than 20 K/h, for example 0.5 to 20 K/h and frequently 1 to 15 K/h. Advantageously, the controlled cooling will be carried out as the crystallization starts. However, it is also possible to cool more rapidly, in which case the crystallizate will be moved over a prolonged period in the mother liquor, i.e. until the desired crystallization time is achieved, before being isolated.

To improve the purity, the crystallization can be carried out in such a way that the solution of the phenyluracil is first cooled down until part or all of the phenyluracil has crystallized out, then reheated in order to incipiently dissolve the crystallizate, but without complete dissolution of the crystallizate taking place, and subsequently cooling the solution again. As regards the temperatures and the cooling rates, what has been said above also applies here analogously.

The crystallization of form II can be promoted or accelerated by seeding with seed crystals of form II, for example by adding seed crystals of form II before or during the crystallization process.

In the event that seed crystals are added during the crystallization process, they typically amount to 0.001 to 10% by weight, frequently 0.005 to 5% by weight, in particular 0.01 to 1% by weight and specifically 0.05 to 0.5% by weight, based on the dissolved phenyluracil I.

In the event that the crystallization is carried out in the presence of seed crystals of form II, these are preferably only added at a temperature at which the saturation concentration of the phenyluracil I in the respective solvent has been attained, i.e. at, or below, the temperature at which the dissolved amount of phenyluracil I in the solvent in question forms a saturated solution. The temperature dependence of the saturation concentration in a solvent can be determined by the skilled worker in routine experiments. Frequently, the seed crystals are added when the temperature of the solution is not more than 60° C. Preferably, the solution is left to cool to temperatures of below 30° C., in particular of 25° C. or less, for example to temperatures in the range of from 0° C. to 25° C., after addition of the seed crystals, before the resulting crystalline material is separated from the mother liquor in order to isolate form II of the phenyluracil I. Cooling in the presence of seed crystals can be performed in a controlled fashion at a cooling rate of, as a rule, not more than 30 K/h, for example 1 to 30 K/h, frequently 2 to 20 K/h and in particular 3 to 15 K/h, or in a noncontrolled fashion.

Here too, reheating to incipiently dissolve the crystallizate, followed by renewed cooling, as described above, may lead to an improved product purity.

It has proved advantageous to move the crystalline material for some time at temperatures below the crystallization temperature, for example in the range of from 0 to 35° C., in the mother liquor, for example 1 h to 3 h, in order to ensure complete crystallization into form II. The total time from the beginning of the cooling process to the isolation of the crystals by separation of the mother liquor will then be in the abovementioned ranges.

As an alternative, crystallization can also be brought about by addition of an anhydrous nonpolar solvent L2, for example of 5 to 60% by volume, in particular 20 to 55% by volume and specifically of 30 to 50% by volume, based on the volume of the solvent, or solvent mixture, used for dissolving the phenyluracil I. Preferably, the addition of the nonpolar solvent L2 is effected over a prolonged period, for example over a period of 30 min to 10 h, in particular over a period of from 1 h to 8 h.

In particular, it is possible to combine the addition of the nonpolar solvent and the addition of seed crystals with one another. The addition of the nonpolar solvent may be effected in the form of pure nonpolar solvent or in the form of a mixture of nonpolar solvent with one of the abovementioned solvents L1, in particular in admixture with the solvent employed for the dissolving process. Examples of nonpolar solvents are aliphatic and cycloaliphatic hydrocarbons such as pentane, hexane, cyclohexane, isohexane, heptane, octane, decane, and haloaromatics such as chlorobenzene, dichlorobenzene or mixtures of these.

Obtaining the form II from the crystallizate, i.e. the removal of form II from the mother liquor, is successfully accomplished by conventional techniques for separating solid constituents from fluids, for example by filtration, centrifugation or decanting. As a rule, the isolated solid will be washed, for example with the solvent used for the crystallization, with water, or with a mixture of the organic solvent used for the crystallization and water. Washing can be effected in one or more steps, the last wash step frequently being performed with water. Washing is typically effected at temperatures of below 30° C., frequently below 25° C. and in particular below 20° C., in order to keep the loss of product of interest as low as possible. Thereafter, the resulting form II may be dried and then processed. Frequently, however, the moist active ingredient obtained after washing, in particular water-moist active ingredient, will be processed directly.

The inventive crystallization generates the form II with a phenyluracil I content of at least 94% by weight, in particular at least 96% by weight. The content of form II, based on the total amount of phenyluracil I, is typically at least 90%, frequently at least 95% and in particular at least 98%.

The preparation of the 2-chloro-5-[3,6-dihydro-2,6-dioxo-4-(trifluoromethyl)-1(2H)-pyrimidinyl]-4-fluoro-N-[[methyl(1-methylethyl)amino]sulfonyl]benzamide employed as a starting material for the preparation of form II can be accomplished by the methods described in WO 01/083459, WO 03/097589, WO 05/054208, WO 06/097589 and PCT/EP 2006/062414, which are hereby incorporated herein in their entirety by reference.

It is especially preferred to prepare the phenyluracil I by the following methods:
1) Conversion of 2-chloro-5-[3,6-dihydro-2,6-dioxo-4-(trifluoromethyl)-1(2H)-pyrimidinyl]-4-fluorobenzoic acid into its acid chloride or the corresponding anhydride and subsequent conversion of the corresponding activated acid derivative with N-methyl-N-(1-methylethyl)sulfamoylamide, for example:

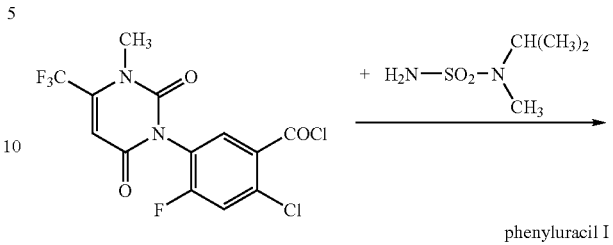

phenyluracil I

This reaction is usually carried out at temperatures of from 20° C. to the boiling point of the reaction mixture in an organic solvent in the presence of a base and, if appropriate, of a catalyst [cf., for example, WO 01/083459, WO 03/097589 and also WO 04/039768].

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide, dimethylformamide and dimethylacetamide. Mixtures of the above-mentioned solvents may also be employed.

Bases which are suitable are, generally, inorganic bases such as alkali metal and alkaline-earth metal hydroxides such as lithium hydroxide, sodium hydroxide, potassium hydroxide and calcium hydroxide, alkali metal and alkaline-earth metal oxides such as lithium oxide, sodium oxide, calcium oxide and magnesium oxide, alkali metal and alkaline-earth metal hydrides such as lithium hydride, sodium hydride, potassium hydride and calcium hydride, alkali metal amides such as lithium amide, sodium amide and potassium amide, alkali metal and alkaline-earth metal carbonates such as lithium carbonate, potassium carbonate and calcium carbonate and also alkali metal bicarbonates such as sodium bicarbonate, organometallic compounds, in particular alkali metal alkyls such as methyllithium, butyllithium and phenyllithium, alkyl magnesium halides such as methyl magnesium chloride and alkali metal and alkaline-earth metal alkoxides such as sodium methoxide, sodium ethoxide, potassium ethoxide, potassium tert-butoxide, potassium tert-pentoxide and dimethoxymagnesium, furthermore organic bases, for example tertiary amines such as trimethylamine, triethylamine, diisopropylethylamine and N-methylpiperidine, pyridine, substituted pyridines such as collidine, lutidine and 4-dimethylaminopyridine, and bicyclic amines.

The bases are generally employed in catalytic or equimolar amounts, but they may also be used in an excess or, if appropriate, as solvents.

The starting materials are generally reacted with each other in equimolar amounts. It may be advantageous to employ one of the starting materials in an excess.
2) Methylation of 2-chloro-5-[3,6-dihydro-2,6-dioxo-4-(trifluoromethyl)-1(2H)-pyrimidinyl]-4-fluoro-N-[[methyl(1-methylethyDamino]sulfonyl]benzamide (hereinbelow "NH-uracil") with a methylating agent C:

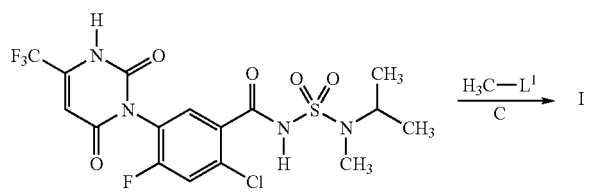 

The group L¹ represents a nucleophilic leaving group, preferably halogen such as chlorine, bromine or iodine, $C_1$-$C_6$-alkyl sulfate such as methyl sulfate, $C_1$-$C_6$-alkyl-sulfonyloxy such as methylsulfonyloxy, $C_1$-$C_6$-haloalkylsulfonyloxy such as trifluoro-methylsulfonyloxy or phenylsulfonyloxy; very preferably $C_1$-$C_6$-alkyl sulfate.

Suitable methylating agents C are methyl halides such as methyl iodide, methyl bromide, methyl chloride, dimethyl sulfate, methyl $C_1$-$C_6$-haloalkylsulfonate, or methyl phenylsulfonate, with methyl halides and dimethyl sulfate being especially preferred; dimethyl sulfate is extraordinarily preferred.

The methylating agent C can be employed either in an equimolar amount based on the NH-uracil, but also in a substoichiometric amount or in an excess.

Process (2) is usually carried out in the presence of a base, with all customary organic and inorganic bases being suitable, for example the bases mentioned in process (1). Preferred bases are selected among alkali metal and alkaline-earth metal hydroxides such as lithium hydroxide, sodium hydroxide, potassium hydroxide and calcium hydroxide, alkali metal and alkaline-earth metal oxides such as lithium oxide, sodium oxide, calcium oxide and magnesium oxide, alkali metal and alkaline-earth metal carbonates such as lithium carbonate, sodium carbonate, potassium carbonate and calcium carbonate and also alkali metal bicarbonates such as sodium bicarbonate. In an especially preferred embodiment, sodium hydroxide or potassium hydroxide is employed as the base. The bases are generally employed in equimolar amounts based on the NH-uracil, but they may also be used in catalytic amounts, in an excess or, if appropriate, as the solvent.

In a very preferred variant of process (2), the pH is kept in a range of from 1 to 6 during all of the reaction by the continuous or portionwise addition of base. "Portionwise addition of base" means that the addition of the base during the conversion is performed in individual portions, i.e. in at least 2 portions, or in more, up to many, portions, or continuously.

To carry out the reaction, the NH-uracil, the methylating agent C and, if appropriate, the base, may be introduced separately, simultaneously or in succession into the reaction vessel and reacted.

In accordance with a first embodiment of process (2), the conversion of the NH-uracil with the methylating agent C is performed in an organic solvent.

Suitable solvents for these reactions are, depending on the temperature range, aliphatic, cycloaliphatic or aromatic hydrocarbons such as pentane, hexane, cyclopentane, cyclohexane, toluene, xylene, chlorinated aliphatic and aromatic hydrocarbons such as dichloromethane, trichloromethane, 1,2-dichloroethane, 1,1,2,2-tetrachloroethane, chlorobenzene, 1,2-, 1,3- or 1,4-dichlorobenzene, chlorotoluenes, dichlorotoluenes, open-chain dialkyl ethers such as diethyl ether, di-n-propyl ether, di-n-isopropyl ether, methyl tert-butyl ether, cyclic ethers such as tetrahydrofuran, 1,4-dioxane, anisole, glycol ethers such as dimethyl glycol ether, diethyl glycol ether, diethylene glycol dimethyl ether, diethylene glycol diethyl ether, $C_1$-$C_4$-alcohols such as methanol, ethanol, n-propanol, isopropanol, n-butanol, $C_1$-$C_6$-alkyl esters of aliphatic carboxylic acids such as methyl acetate, ethyl acetate or n-butyl acetate; ketones such as acetone, methyl ethyl ketone, methyl isopropyl ketone, methyl isobutyl ketone, butanone, carbonates such as diethyl carbonate and ethylene carbonate, N,N-dialkyl amides such as N,N-dimethylformamide or N,N-dimethyl-acetamide, N-alkyllactams such as N-methylpyrrolidone, sulfoxides such as dimethyl sulfoxide, tetraalkylureas such as tetramethylurea, tetraethylurea, tetrabutylureas, dimethylethyleneurea, dimethylpropyleneurea, or mixtures of these solvents.

Preferred solvents are N,N-dialkylamides such as N,N-dimethylformamide, N-alkyllactams such as N-methylpyrrolidone, ketones such as acetone, aromatic hydrocarbons such as toluene, chlorinated aliphatic and aromatic hydrocarbons such as dichloromethane or chlorobenzene, cyclic ethers such as tetrahydrofuran, $C_1$-$C_6$-alkyl esters of aliphatic carboxylic acids such as ethyl acetate, butyl acetate, or mixtures of these solvents.

The methylation of the NH-uracil is preferably accomplished at temperatures between −5° C. and 100° C. The reaction time can be determined by the skilled worker in a manner known per se by routine methods such as thin-layer chromatography or HPLC.

In another variant of process (2a), the conversion can also be carried out in a multiphase system. This variant is preferred.

As regards methylating agent C, pH, base, temperature and pressure, what has been said above also applies here.

In accordance with a second, preferred embodiment of process (2), the reaction of the NH-uracil with the methylating agent C is carried out in an aqueous-organic multiphase system in the presence of one or more phase transfer catalysts.

Examples of phase transfer catalysts are quaternary ammonium salts, phosphonium salts, crown ethers or polyglycols. Preferred suitable quaternary ammonium salts comprise, for example, tetra($C_1$-$C_{18}$)alkylammonium halides and N-benzyltri($C_1$-$C_{18}$)-alkylammonium halides. Preferred suitable phosphonium salts comprise, for example, $C_1$-$C_{18}$-alkyltriphenylphosphonium chlorides, $C_1$-$C_{18}$-alkyltriphenylphosphonium bromides, $C_1$-$C_{18}$-alkyltriphenylphosphonium acetates, tetra($C_1$-$C_{18}$)alkylphosphonium chlorides or tetra ($C_1$-$C_{18}$)alkylphosphonium bromides, tetraphenylphosphonium chloride or tetraphenylphosphonium bromide, benzyltriphenylphosphonium chloride or benzyltriphenylphosphonium bromide. Preferred suitable crown ethers comprise, for example, 18-crown-6, dibenzo-18-crown-6. Preferred suitable polyglycols comprise, for example, diethylene glycol dibutyl ether (=butyldiglyme), tetraethylene glycol dimethyl ether (=tetraglyme), triethylene glycol dimethyl ether (=triglyme), polyglycol dimethyl ether. As a rule, the phase transfer catalyst is employed in an amount of up to 20 mol % based on the NH-uracil.

The multiphase system comprises an aqueous phase and at least one organic liquid phase. In addition, solid phases may also be present.

The aqueous phase is preferably a solution which comprises the base, in particular an aqueous solution of alkali metal or alkaline-earth metal hydroxides (such as lithium hydroxide, sodium hydroxide, potassium hydroxide and calcium hydroxide), alkali metal or alkaline-earth metal carbonates (such as lithium carbonate, sodium carbonate, potassium carbonate and calcium carbonate) or alkali metal bicarbonates (such as sodium bicarbonate) in water. It is especially preferred to use alkali metal or alkaline-earth metal hydroxides, very preferably sodium hydroxide.

The base(s) is/are generally employed in equimolar amounts based on the NH-uracil, but may also be used in catalytic amounts, in an excess or, if appropriate, as the solvent. It is preferred to employ at least one equimolar amount of base, based on the NH-uracil.

Suitable solvents for the organic phase, depending on the temperature range, are preferably aliphatic, cycloaliphatic or aromatic hydrocarbons such as pentane, hexane, cyclopentane, cyclohexane, toluene, xylene, chlorinated aliphatic and aromatic hydrocarbons such as dichloromethane, trichloromethane, 1,2-dichloroethane, 1,1,2,2-tetrachloroethane, chlorobenzene, 1,2-, 1,3- or 1,4-dichlorobenzene, chlorotoluenes, dichlorotoluenes, open-chain dialkyl ethers such as diethyl ether, di-n-propyl ether, di-n-isopropyl ether, methyl tert-butyl ether, cyclic ethers such as tetrahydrofuran (THF) and anisole, $C_1$-$C_6$-alkyl esters of aliphatic carboxylic acids such as methyl acetate, ethyl acetate or n-butyl acetate, or mixtures of these solvents. Preferred solvents for the organic phase are ethyl acetate, n-butyl acetate, chlorobenzene, THF, toluene, or mixtures of these solvents; ethyl acetate, n-butyl acetate, chlorobenzene and THF mixtures, and also toluene and THF mixtures, are very preferred.

Solid phases may occur during the conversion, for example when the NH-uracil, the methylating agent C, the base and/or the phase transfer catalyst are not fully dissolved.

In a preferred embodiment, the multiphase system when used as the aqueous phase consists of aqueous sodium hydroxide solution, and when used as the organic phase it consists of toluene and tetrahydrofuran, or dichloromethane and tetrahydrofuran, chlorobenzene and tetrahydrofuran, or of ethyl acetate or n-butyl acetate.

To carry out the conversion, the NH-uracil, the methylating agent C, the base and, if appropriate, the phase transfer catalyst can be introduced separately, simultaneously or in succession into the reaction vessel and reacted therein.

When using a two-phase system, the phases will, as a rule, be separated before form II is crystallized. It is especially preferred to dry the resulting product by drying methods known to the skilled worker, for example by azeotroping the water off together with part of the organic solvent, before carrying out the crystallization.

The figures and examples which follow are intended to illustrate the invention and are not taken to be limiting.

FIG. 1 shows an X-ray powder diffractogram of form II. The X-ray diffractogram of form II was recorded with a diffractometer type D-5000 from Bruker-AXS in reflection geometry in the range of 2θ=4°-35° with a step width of 0.02° using the Cu—$K_\alpha$ radiation at 25° C. The reported interplanar spacings d were calculated from the determined 2θ values.

Figure 2:
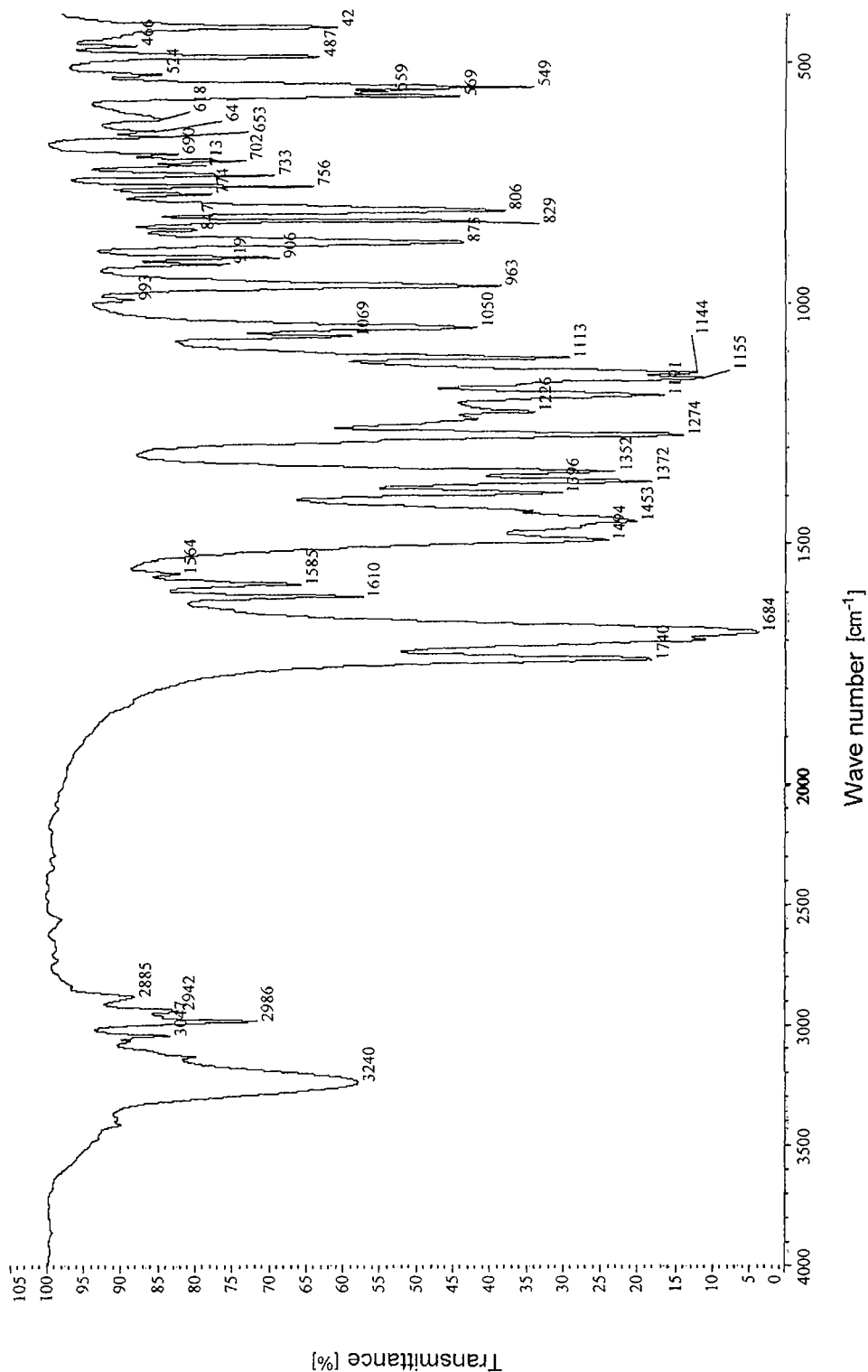

FIG. 2 shows an IR spectrum of form II. The IR spectra were recorded by means of FTIR spectrometers "Nicolet Magna 550" and "Nicolet Magna 750" from Thermo Electron Corp./USA in the wave number range of 400-4000 $cm^{-1}$ at a resolution of 4 $cm^{-1}$ (32 scans). The test specimens were KBr pellets.

The melting points and melting heats were determined via DSC using a Mettler Toledo DSC 25 apparatus from Mettler at a heating rate of 5 K/min in the range of from ±5° C. to +80° C. The sample amount was 5 to 10 mg.

The crystallographic data of form II (Table 1) were determined using a single-crystal diffractometer from Bruker ("Bruker P4") using Cu—$K_\alpha$ radiation.

Preparation of Form II of the Phenyluracil I by Crystallization of the Amorphous Form I from an Organic Solvent with Removal of the Solvent (General Procedure)

1 g of amorphous phenyluracil I was dissolved at room temperature in 25 ml of the solvent stated in each case. The resulting solution was warmed to the temperature detailed in Table 3 and left at this temperature, a stream of nitrogen passing over the solution in order to evaporate the solvent. After removal of the solvent, the mixture was cooled to ambient temperature, and the crystalline material was isolated and analyzed by means of DSC and/or by means of X-ray powder diffractometry (XRD). Form II was obtained in all cases.

TABLE 3

| Example | Solvent | T [° C.] | XRD[1] | DSC peak [° C.] |
|---|---|---|---|---|
| 1 | acetone | 35 | n.a. | 187 |
| 2 | isopropanol | 35 | + | 183, 187 |
| 3 | isopropanol | 70 | n.a. | 190 |
| 4 | toluene | 35 | + | 189 |
| 5 | toluene | 80 | + | 189 |
| 6 | methyl isobutyl ketone | 100 | n.a. | 189 |
| 7 | 1-pentanol | 50 | n.a. | 188 |
| 8 | 1-pentanol | 120 | + | 178 |
| 9 | nitromethane | 40 | + | 186 |

[1]X-ray powder diffractogram: + = measured; n.a. not measured

EXAMPLE 10

1 g of amorphous phenyluracil I was dissolved at room temperature in 25 ml of acetonitrile. The clear solution was left to stand for one week at ambient temperature, without covering, during which process most of the solvent evaporated and a crystalline white precipitate remained. The DSC peak at 187° C. confirmed the presence of form II.

EXAMPLE 11

Preparation of Form II of the Phenyluracil I by Crystallization of the Amorphous form I from Acetone 0.2 g of the amorphous form I was dissolved in 10 drops of acetone at 22° C., with stirring. Thereafter, stirring was continued for 3 minutes, and a first turbidity developed, which intensified over the next 30 minutes with formation of a precipitate. The precipitate was allowed to settle out (30 min.) and the acetone was then removed in vacuo; this gave 0.191 g (96% of theory) of form II with a melting point of 180-184° C.

EXAMPLE 12

Preparation of Form II of the Phenyluracil I by Crystallization from the Reaction Solution 50.0 g (0.098 mol) of 2-chloro-5-[3,6-dihydro-2,6-dioxo-4-(trifluoromethyl)-1(2H)-pyrimidinyl]-4-fluoro-N-{[methyl(1-methylethyl)amino]sulfonyl}benzamide, 3.2 g (0.0089 mol) of tetrabutylammonium bromide (=TBAB) and 15.1 g (0.12 mol) of dimethyl sulfate were introduced into the reaction vessel at 25° C. in a mixture of toluene, water and THF, and the mixture was heated to 40° C. Thereafter, a pH of 5.3-5.5 was established in the reaction mixture by addition of aqueous 10% strength NaOH solution. During the entire duration of the reaction, more aqueous 10% strength NaOH solution was added so that the pH during the entire course of the reaction was constantly at the pH which had been established beforehand. After the reaction had ended, stirring of the reaction mixture was continued for 3.5 h at 40° C. The phases were subsequently separated.

55 to 60% of the solvent employed were removed from the resulting solution by distillation under atmospheric pressure, giving a hot solution of the title compound in toluene. The solution was subsequently cooled to 70° C. and then, within 5 h, and at a constant cooling rate, to 20° C., and stirring was continued for 3 h at 20° C. The solid which had precipitated was filtered off with suction and dried. This gave 42.6 g (84.0%) of the title compound as form II with an active ingredient content of 96.8%.

Like form I, form II is suitable as herbicide, but is superior to the former in terms of activity. The invention therefore also relates to plant protection compositions comprising the crystalline form II and adjuvants which are conventionally used in the formulation of plant protection compositions, in particular plant protection compositions in the form of aqueous or nonaqueous suspension concentrates. The invention also relates to a method of controlling undesired vegetation, which comprises allowing form II of the phenyluracil, preferably as a suitable active substance preparation, to act on plants, their environment and/or on seeds.

The herbicidal compositions comprising form II effect a very good control of vegetation on noncrop areas, especially at high application rates. In crops such as wheat, rice, maize, soya and cotton, they are active against broad-leaved weeds and grass weeds without inflicting substantial damage to the crop plants. This effect is particularly observed at low application rates.

Depending on the application method in question, form II, or the herbicidal compositions comprising it, can additionally be employed in a further number of crop plants to remove undesired plants. Crops which are suitable are, for example, the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N. rustica), Olea europaea, Oryza sativa, Phaseolus lunatus, Phaseolus vulgaris, Picea abies, Pinus* spec., *Pisum sativum, Prunus armeniaca, Prunus avium, Prunus cerasus, Prunus dulcis, Prunus domesticua, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera* and *Zea mays.*

In addition, form II, or the herbicidal compositions comprising it, can also be used in crops which tolerate the effect of herbicides as the result of breeding, including genetic engineering methods.

Furthermore, form II, or the herbicidal compositions comprising it, can also be used in crops which tolerate attack by insects or fungi as the result of breeding, including genetic engineering methods.

Moreover, it has been found that form II is also suitable for the defoliation and desiccation of plant parts, for which crops plants such as cotton, potato, oilseed rape, sunflower, soybean or field beans, in particular cotton, are suitable. In this regard, there have been found compositions for the desiccation and/or defoliation of plants, processes for the preparation of these compositions and methods of desiccating and/or defoliating plants using form II.

As desiccants, form II is particularly suitable for desiccating the aerial parts of crop plants such as potato, oilseed rape, sunflower and soybean. This makes possible the fully mechanical harvesting of these important crop plants. Also of economic interest is to facilitate harvesting, which is made possible by concentrating within a certain period of time the dehiscence, or reduction of adhesion to the tree, in citrus fruit, olives or other species and varieties of pome fruit, stone fruit and nuts. The same mechanism, i.e. the promotion of the development of abscission tissue between fruit part or leaf part and shoot part of the plants is also essential for the controlled defoliation of useful plants, in particular cotton. Moreover, a shortening of the time interval within which the individual cotton plants mature leads to an increased fiber quality after harvesting.

Moreover, it has been found that form II is also suitable for the control of conifers, in particular of conifer seedlings which grow naturally, specifically for the control of pine seedlings which grow naturally.

Form II is also suitable for the control of weeds in crop plants such as, for example, soybean, cotton, oilseed rape, flax, lentils, rice, sugar beet, sunflower, tobacco and cereals, such as, for example maize or wheat.

Form II or the herbicidal compositions comprising it can be applied, for example in the form of directly sprayable aqueous solutions, powders, suspensions, also highly concentrated aqueous, oily or other suspensions, oil suspensions, pastes, dusts, tracking powders or granules, by means of spraying, atomizing, dusting, tracking or drenching. The use forms depend on the intended purposes; in any case, this should ensure the finest possible distribution of the active substances according to the invention.

The herbicidal compositions comprise a herbicidally active amount of form II and auxiliaries and carriers conventionally used for the formulation of plant protection products.

Carriers which are suitable are, in principle, all solid substances which are conventionally employed in plant protection products, in particular in herbicides. Examples of solid carriers are mineral earths such as silica gels, silicates, talc, kaolin, attaclay, limestone, lime, chalk, boll, loess, clay, dolomite, diatomaceous earth, calcium sulfate, magnesium sulfate, magnesium oxide, ground synthetic materials, fertilizers such as, for example, ammonium sulfate, ammonium phosphate, ammonium nitrate, ureas and products of vegetable origin such as cereal meal, tree bark meal, wood meal and nutshell meal, cellulose powders and other solid carriers.

In the case of liquid formulations of form II, the compositions have a liquid phase. Suitable as the liquid phase are, in principle, water and those organic solvents in which form II is not soluble or only sparingly soluble, for example those in which the solubility of form II of the phenyluracil I at 25° C. and 1013 mbar is not more than 1% by weight, in particular not more than 0.1% by weight and specifically not more than 0.01% by weight.

Preferred liquid phases are, in particular, water and aqueous solvents, i.e. solvent mixtures which, besides water, also comprise up to 30% by weight, but preferably not more than 10% by weight, based on the total amount of water and solvent, of one or more water-miscible organic solvents, for example water-miscible ethers such as tetrahydrofuran, methyl glycol, methyl diglycol, alkanols such as methanol, ethanol, isopropanol, or polyols such as glycol, glycerol, diethylene glycol, propylene glycol and the like.

Preferred liquid phases are, furthermore, nonaqueous organic solvents in which the solubility of form II of the phenyluracil I at 25° C. and 1013 mbar is not more than 1% by weight, in particular not more than 0.1% by weight and specifically not more than 0.01% by weight. These include, in particular, aliphatic and cycloaliphatic hydrocarbons and oils, in particular those of vegetable origin, furthermore $C_1$-$C_4$-alkyl esters of saturated or unsaturated fatty acids or fatty acid mixtures, in particular the methyl esters, for example methyl oleate, methyl stearate, rapeseed oil methyl esters, but also paraffinic mineral oils and the like.

Typical auxiliaries comprise surface-active substances, in particular the wetters and dispersants/dispersion aids which are conventionally employed in plant protection compositions, furthermore additives which modify the viscosity (thickeners), antifoam agents, antifreeze agents, pH regulators, stabilizers, anticaking agents and biocides (preservatives).

The invention relates in particular to compositions for plant protection in the form of an aqueous suspension concentrate (SC). Such suspension concentrates comprise form II of the phenyluracil I in a finely divided particulate form, where the particles of form II are suspended in an aqueous phase. The size of the active substance particles, i.e. the size not exceeded by 90% by weight of the active substance particles, is typically below 30 μm, in particular below 20 μm. Advantageously, at least 40% by weight and in particular at least 60% by weight of the particles in the SCs according to the invention have diameters of below 2 μm.

Besides the active substance, aqueous suspension concentrates typically comprise surface-active substances and, if appropriate, antifoam agents, thickeners, antifreeze agents, stabilizers (biocides), pH regulators and anticaking agents.

The amount of active substance, i.e. the total amount of phenyluracil of the form II and, if appropriate, further active substances in such SCs are usually in the range of from 10 to 70% by weight, in particular in the range of from 20 to 50% by weight, based on the total weight of the suspension concentrate.

Suitable surface-active substances are, preferably, anionic and nonionic surfactants. Other suitable surface-active substances are protective colloids. As a rule, the amount of surface-active substances will amount to from 0.5 to 30% by weight, in particular 1 to 20% by weight, based on the total weight of the aqueous SCs according to the invention. Preferably, the surface-active substances comprise at least one anionic surface-active substance and at least one nonionic surface-active substance, the weight ratio of anionic to nonionic surface-active substance being typically in the range of from 10:1 to 1:10.

Examples of anionic surface-active substances (surfactants) include alkylaryl-sulfonates, phenylsulfonates, alkyl sulfates, alkylsulfonates, alkyl ether sulfates, alkylaryl ether sulfates, alkyl polyglycol ether phosphates, polyarylphenyl ether phosphates, alkyl sulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde or with formaldehyde and phenol and, if appropriate, urea, and condensates of phenolsulfonic acid, formaldehyde and urea, lignin-sulfite waste liquor and lignosulfonates, alkyl phosphates, alkylaryl phosphates, for example tristyryl phosphates, and also polycarboxylates such as, for example, polyacrylates, maleic anhydride/olefin copolymers (for example Sokalan® CP9, BASF), including the alkali metal, alkaline-earth metal, ammonium and amine salts of the above-mentioned substances. Preferred anionic surface-active substances are those which contain at least one sulfonate group and in particular their alkali metal salts and their ammonium salts.

Examples of nonionic surface-active substances comprise alkylphenol alkoxylates, alcohol alkoxylates, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers (polyethylene oxide/polypropylene oxide block copolymers) and their mixtures. Preferred nonionic surface-active substances are fatty alcohol ethoxylates, alkyl polyglycosides, glycerol fatty acid esters, castor oil alkoxylates, fatty acid alkoxylates, fatty acid amide alkoxylates, lanolin ethoxylates, fatty acid polyglycol esters and ethylene oxide/propylene oxide block copolymers, and mixtures of these.

Protective colloids are, typically, water-soluble amphiphilic polymers. Examples are proteins and denatured proteins such as casein, polysaccharides such as water-soluble starch derivatives and cellulose derivatives, in particular hydrophobically modified starches and celluloses, furthermore polycarboxylates such as polyacrylic acid and acrylic acid copolymers, polyvinyl alcohol, polyvinyl pyrrolidone, vinylpyrrolidone copolymers, polyvinylamines, polyethyleneimines, and polyalkylene ethers.

Viscosity-modifying additives (thickeners) which are suitable for the aqueous SCs according to the invention are, in particular, compounds which impart a modified flowing behavior to the formulation, for example a high viscosity in the static state and low viscosity in the state of motion. Suitable compounds are, in principle, all those employed in suspension concentrates for this purpose. Substances to be mentioned are, for example, inorganic substances, for example layer silicates and organic modified layer silicates such as bentonites or attapulgites (for example Attaclay® from Engelhardt), and organic substances such as polysaccharides and heteropolysaccharides such as Xanthan Gum® (Kelzan® from Kelco), Rhodopol® 23 (Rhone Poulenc) or Veegum® (from R.T. Vanderbilt), with Xanthan-Gum® being used by preference. The amount of the viscosity-modifying additives is frequently 0.1 to 5% by weight, based on the total weight of the SCs.

Antifoam agents which are suitable for the aqueous SCs according to the invention are, for example, silicone emulsions which are known for this purpose (Silikon® SRE, from Wacker or Rhodorsil® from Rhodia), long-chain alcohols, fatty acids and their salts, antifoams of the aqueous wax dispersion type, solid antifoams (known as Compounds), organofluorine compounds and mixtures of these. The amount of antifoam agents is typically 0.1 to 1% by weight, based on the total weight of the SCs.

Preservatives may also be added to the suspension concentrates according to the invention for the purposes of stabilizing them. Suitable preservatives are those based on isothiazolones, for example Proxel® from ICI or Acticide® RS from Thor Chemie or Kathon® MK from Rohm & Haas. The amount of preservative is typically 0.05 to 0.5% by weight, based on the total weight of the SCs.

Suitable antifreeze agents are liquid polyols, for example ethylene glycol, propylene glycol or glycerol, and also urea.

The amount of antifreeze agents is, as a rule, 1 to 20% by weight, in particular 5 to 10% by weight, based on the total weight of the aqueous suspension concentrate.

If appropriate, the aqueous SCs according to the invention may comprise buffers to regulate the pH. Examples of buffers are alkali metal salts of weak inorganic or organic acids such as, for example, phosphoric acid, boric acid, acetic acid, propionic acid, citric acid, fumaric acid, tartaric acid, oxalic acid and succinic acid.

If the formulations of the crystalline modifications of form II are employed for the treatment of seed, they may comprise further customary constituents as are employed in seed treatment, for example seed dressing or coating. Besides the above-mentioned constituents, these include in particular colorants, adhesives, fillers and plasticizers.

Colorants which are suitable are all dyes and pigments conventionally used for such purposes. Both pigments, which are sparingly soluble in water, and dyes, which are water-soluble, may be used. Examples which may be mentioned are the dyes and pigments known under the names Rhodamin B, C. I. Pigment Red 112 and C. I. Solvent Red 1, Pigment blue 15:4, Pigment blue 15:3, Pigment blue 15:2, Pigment blue 15:1, Pigment blue 80, Pigment yellow 1, Pigment yellow 13, Pigment red 48:2, Pigment red 48:1, Pigment red 57:1, Pigment red 53:1, Pigment orange 43, Pigment orange 34, Pigment orange 5, Pigment green 36, Pigment green 7, Pigment white 6, Pigment brown 25, Basic violet 10, Basic violet 49, Acid red 51, Acid red 52, Acid red 14, Acid blue 9, Acid yellow 23, Basic red 10, Basic red 108. The amount of colorant will usually not exceed 20% by weight of the formulation and is preferably in the range of from 0.1 to 15% by weight, based on the total weight of the formulation.

Stickers which are suitable are all customary binders which can be employed in seed-dressing products. Examples of suitable binders comprise thermoplastic polymers such as polyvinylpyrrolidone, polyvinyl acetate, polyvinyl alcohol and tylose, furthermore polyacrylates, polymethacrylates, polybutenes, polyisobutenes, polystyrene, polyethyleneamines, polyethylene amides, the abovementioned protective colloids, polyesters, polyether esters, polyanhydrides, polyester urethanes, polyester amides, thermoplastic polysaccharides, for example cellulose derivatives such as cellulose esters, cellulose ethers, cellulose ether esters, including methylcellulose, ethylcellulose, hydroxymethylcellulose, carboxymethylcellulose, hydroxypropylcellulose and starch derivatives and modified starches, dextrins, maltodextrins, alginates and chitosans, furthermore fats, oils, proteins, including casein, gelatin and zein, gum arabic, shellac. Preferably, the stickers are tolerated by plants, i.e. they have no, or no substantial, phytotoxic effects. The stickers are preferably biodegradable. The sticker is preferably selected so that it acts as the matrix for the active components of the formulation. The amount of sticker will usually not exceed 40% by weight of the formulation and is preferably in the range of from 1 to 40% by weight and in particular in the range of from 5 to 30% by weight, based on the total weight of the formulation.

Besides the sticker, the seed treatment formulation may also comprise inert fillers. Examples are the abovementioned solid carriers, in particular finely divided inorganic materials such as clays, chalk, bentonite, kaolin, talc, perlite, mica, silica gel, diatomaceous earth, quartz powder, montmorillonite, but also finely divided organic materials such as wood meal, cereal meal, active charcoal and the like. The amount of filler will preferably be selected so that the total amount of filler does not exceed 75% by weight based on the total weight of all nonvolatile components of the formulation. Frequently, the amount of filler will be in the range of from 1 to 50% by weight, based on the total weight of all nonvolatile components of the formulation.

In addition, the seed treatment formulation may also comprise a plasticizer which increases the flexibility of the coating. Examples of plasticizers are oligomeric polyalkylene glycols, glycerol, dialkyl phthalates, alkyl benzyl phthalates, glycol benzoates and comparable compounds. The amount of plasticizer in the coating is frequently in the range of from 0.1 to 20%, based on the total weight of all nonvolatile components of the formulation.

In particular, the invention also relates to plant protection compositions in the form of a nonaqueous suspension concentrate. Such suspension concentrates comprise form II of the phenyluracil I in a finely divided particulate form, the particles of form II being suspended in a nonaqueous phase. The size of the active substance particles, i.e. the size which is not exceeded by 90% by weight of the active substance particles, is typically below 30 µm, in particular below 20 µm. Advantageously, at least 40% by weight and in particular at least 60% by weight of the particles in the nonaqueous SCs have diameters of below 2 µm.

Besides the active substance, nonaqueous suspension concentrates typically comprise surface-active substances and, if appropriate, antifoam agents, thickeners, antifreeze agents, stabilizers (biocides), pH regulators and anticaking agents.

The amount of active substance, i.e. the total amount of phenyluracil I in the form II and, if appropriate, further active substances, in such nonaqueous SCs is usually in the range of from 10 to 70% by weight, in particular in the range of from 20 to 50% by weight, based on the total weight of the nonaqueous suspension concentrate.

Suitable surface-active substances are, preferably, the abovementioned anionic and nonionic surfactants. As a rule, the amount of surface-active substances will amount to from 1 to 30% by weight, in particular 2 to 20% by weight, based on the total weight of the nonaqueous SCs according to the invention. Preferably, the surface-active substances comprise at least one anionic surface-active substance and at least one nonionic surface-active substance, the weight ratio of anionic to nonionic surface-active substance being typically in the range of from 10:1 to 1:10.

The form II according to the invention may also be formulated as powders, including tracking powders, and dust. Such formulations can be prepared by mixing or concomitantly grinding the form II with a solid carrier and, if appropriate, further auxiliaries.

Form II according to the invention may also be formulated as granules, for example coated granules, impregnated granules and homogeneous granules. Such formulations can be prepared by binding the active substances to solid carriers. Solid carriers are mineral earths such as silicas, silica gels, silicates, talc, kaolin, limestone, lime, chalk, boll, loess, clay, dolomite, diatomaceous earth, calcium sulfate, magnesium sulfate, magnesium oxide, ground synthetic substances, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of form II in the ready-to-use preparations can be varied within wide limits. In general, the formulations comprise approximately from 11 to 98% by weight, preferably from 10 to 95% by weight, based on the total weight of active substances.

The formulation examples which follow illustrate how such preparations are made:

I. 20 parts by weight of form II are mixed thoroughly with 3 parts by weight of the sodium salt of diisobutylnaphthalenesulfonic acid, 17 parts by weight of the sodium salt of a lignosulfonic acid from a sulfite waste liquor and 60 parts by weight of pulverulent silica gel, and the mixture is ground in a hammer mill. This gives a water-dispersible powder which comprises the form II. Finely distributing the mixture in 20 000 parts by weight of water gives a spray mixture which comprises 0.1% by weight of form II.

II. 3 parts by weight of form II are mixed with 97 parts by weight of finely divided kaolin. This gives a dust which comprises 3% by weight of form II.

III. 20 parts by weight of form II are mixed intimately with 2 parts by weight of calcium salt of dodecylbenzenesulfonic acid, 8 parts by weight of fatty alcohol polyglycol ether, 2 parts by weight of the sodium salt of a phenolsulfonic acid/urea/formaldehyde condensate and 68 parts by weight of a paraffinic mineral oil. This gives a stable nonaqueous suspension concentrate of the form II.

IV. 10 parts by weight of form II were formulated as suspension concentrate in a solution of 17 parts by weight of a poly(ethylene glycol)(propylene glycol) block copolymer, 2 parts by weight of a phenolsulfonic acid/formaldehyde condensate and approximately 1 part by weight of other auxiliaries (thickeners, antifoams) in a mixture of 7 parts by weight of propylene glycol and 63 parts by weight of water.

The application of form II or of the herbicidal compositions comprising it is accomplished in the form of aqueous spray mixtures, unless the formulation is ready to use. These aqueous spray mixtures are prepared by dilution with water of the abovementioned formulations which comprise form II of the phenyluracil I. The spray mixtures may also comprise further constituents in dissolved, emulsified or suspended form, for example fertilizers, active substances of other groups of herbicidal or growth-regulatory active substances, further active substances, for example active substances for controlling animal pests or phytopathogenic fungi or bacteria, furthermore mineral salts which are employed for alleviating nutritional and trace element deficiencies, and nonphytotoxic oils or oil concentrates. As a rule, these constituents are added to the spray mixture before, during or after dilution of the formulations according to the invention.

Form II or the herbicidal compositions comprising it can be applied by the pre-emergence or the post-emergence method. If the phenyluracil I is less well tolerated by certain crop plants, application techniques may be employed where the herbicidal compositions are sprayed, with the aid of the spraying apparatus, in such a way that the leaves of the sensitive crop plants ideally do not come into contact with them, while the active substances reach the leaves of undesired plants which grow underneath, or the bare soil surface (post-directed, lay-by).

Depending on the aim of the control measures, the season, the target plants and the growth stage, the application rates of form II are from 0.001 to 3.0, preferably from 0.01 to 1.0 kg/ha active substance (a.s.).

To widen the spectrum of action and to obtain synergistic effects or to increase selectivity, form II can be mixed with a large number of representatives of other groups of herbicidal or growth-regulatory active substances and/or safeners and can be applied together with these. Form II may be employed, or applied, in analogy to the mixtures of phenyluracils I with herbicides, growth regulators and/or safeners, which mixtures have been described in WO 2003/024221, WO 2004/080183, WO 2006/097509 and WO 2007/042447.

Examples of suitable mixing partners are 1,2,4-thiadiazoles, 1,3,4-thiadiazoles, amides, aminophosphoric acid and its derivatives, aminotriazoles, anilides, aryloxy/heteroaryloxyalkanoic acids and their derivatives, benzoic acid and its derivatives, benzothia-diazinones, 2-(hetaroyl/aroyl)-1,3-cyclohexanediones, heteroaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetero-aryloxyphenoxypropionic acid esters, phenylacetic acid and its derivatives, 2-phenyl-propionic acid and its derivatives, pyrazoles, phenylpyrazoles, pyridazines, pyridine-carboxylic acid and its derivatives, pyrimidyl ethers, sulfonamides, sulfonylureas, triazines, triazinones, triazolinones, triazolecarboxamides and uracils. Examples of suitable safeners are (quinoline-8-oxy)acetic acids, 1-phenyl-5-haloalkyl-1H-1,2,4-triazole-3-carboxylic acids, 1-phenyl-4,5-dihydro-5-alkyl-1H-pyrazole-3,5-dicarboxylic acids, 4,5-dihydro-5,5-diary)-3-isoxazolecarboxylic acids, dichloroacetamides, alpha-oximinophenylacetonitriles, acetophenone oximes, 4,6-dihalo-2-phenylpyrimidines, N-[[4-(aminocarbonyl)phenyl]sulfonyl]-2-benzamides, 1,8-napthalamide, 2-halo-4-(haloalkyl)-5-thiazolecarboxylic acids, phosphorothiolates and N-alkyl-O-phenylcarbamates and their agriculturally useful salts, and, with proviso that they have an acid function, their agriculturally useful derivatives, such as amides, esters and thioesters.

Moreover, it may be useful to apply the form II, alone or in combination with other herbicides and/or safeners, jointly as a mixture with yet further plant protection agents, for example with agents for controlling pests or phytopathogenic fungi or bacteria. Also of interest is the miscibility with mineral salt solutions which are employed for alleviating nutritional and trace element deficiencies. Nonphytotoxic oils and oil concentrates may also be added.

USE EXAMPLES

The herbicidal activity of form II was demonstrated by the following greenhouse experiments:

The culture containers used were plastic pots which were filled with soil (for example loamy sand with approximately 3.0% humus) as the substrate. The seeds of the test plants were sown separately for each species.

In the case of the pre-emergence treatment, the active substances, which were suspended in water, were applied directly after sowing, by means of finely distributing nozzles. The containers were irrigated gently to promote germination and growth and subsequently covered with translucent plastic tents until the plants had rooted. This covering brings about a uniform germination of the test plants, unless this has been adversely affected by the active substances.

For the purposes of the post-emergence treatment, the test plants were first grown to a height of 3 to 15 cm, depending on the growth form, and only then treated with the active substances which have been suspended in water. To this end, the test plants were either sown directly and grown in the same containers, or they were first grown separately as seedlings and transplanted into the test containers a few days prior to the treatment.

The plants were kept at temperatures of from 10 to 25° C., or 20 to 35° C., respectively, depending on the species. The test period extended over 2 to 4 weeks. During this period, the plants were tended, and their response to the individual treatments was evaluated.

The evaluation was carried out using a scale of from 0 to 100. 100 means no emergence of the plants, or complete destruction of at least the aerial parts, and 0 means no damage or normal course of growth.

The abovementioned methods were used to compare, in a greenhouse test, form II according to the invention and, as comparison compound, form I, which is disclosed in WO 01/83459, in each case formulated as aqueous suspension concentrate (SC; 100 g/l), if appropriate with the addition of 1 l/ha Rustica Öl®. The suspension concentrates had the following composition:

| | |
|---|---|
| phenyluracil I | 100 g/l |
| 1,2-propylene glycol | 70 g/l |
| dispersant I | 167 g/l |
| dispersant II | 20 g/l |
| xanthan gum | 3 g/l |
| biocide | 1.8 g/l |
| water | to 1 l | dispersant I: EO/PO block copolymer
dispersant II: phenolsulfonic acid/formaldehyde condensate The plants used in the greenhouse experiments belong to the following species:

| Scientific name | English name |
|---|---|
| Ambrosia elatior | common ragweed |
| Capsella bursa-pastoris | shepherdspurse |
| Chenopodium album | common lambsquarters |
| Euphorbia heterophylla | spurge |
| Galium aparine | catchweed bedstraw |
| Glycine max | soybean |
| Helianthus annuus | sunflower |
| Hordeum vulgare | winter barley |
| Kochia scoparia | fireweed |
| Lamium purpureum | purple deadnettle |
| Matricaria inodora | scentless mayweed |
| Mercurialis annua | annual mercury |
| Papaver rhoeas | corn poppy |
| Pharbitis purpurea | common morningglory |
| Polygonum convolvulus | wild buckwheat |
| Salsola kali ssp. ruthenica | russian thistle |
| Secale cereale | winter rye |
| Sida spinosa | prickly mellow |
| Sinapis arvensis | wild mustard |
| Stellaria media | chickweed |
| Thlaspi arvense | frenchweed |
| Triticum aestivum | spring wheat |
| Veronica persicaria | birdseye speedwell |
| Viola arvensis | field violet |

TABLE 4

Comparison of the herbicidal activity of form II with form I, which is disclosed in WO 01/83459, when applied pre-emergence (greenhouse)

| | | Active substance | |
|---|---|---|---|
| Test plants | Application rate (g/ha a.s.) | Form II | Form I |
| | | Damage [%] | |
| Useful plant: | | | |
| Glycine max | 25 | 30 | 70 |
| | 12.5 | 10 | 30 |

TABLE 4-continued

Comparison of the herbicidal activity of form II with form I, which is disclosed in WO 01/83459, when applied pre-emergence (greenhouse)

| | | Active substance | |
|---|---|---|---|
| Test plants | Application rate (g/ha a.s.) | Form II | Form I |
| | | Damage [%] | |
| Harmful plant: | | | |
| Stellaria media | 25 | 100 | 75 |
| | 12.5 | 85 | 65 |
| Ambrosia elatior | 12.5 | 75 | 60 |
| Helianthus annuus | 12.5 | 100 | 70 |
| Euphorbia heterophylla | 12.5 | 100 | 95 |
| | 6.25 | 70 | 40 |
| Mercurialis annua | 6.25 | 100 | 40 |
| Pharbitis purpurea | 6.25 | 100 | 70 |
| Sida spinosa | 12.5 | 100 | 90 |

TABLE 5

Comparison of the herbicidal activity of form II with form I, which is disclosed in WO 01/83459, when applied post-emergence, with addition of 1 l/ha Rustica Öl ® (greenhouse)

| | | Active substance | |
|---|---|---|---|
| Test plants | Application rate (g/ha a.s.) | Form II | Form I |
| | | Damage [%] | |
| Useful plant: | | | |
| Hordeum vulgare | 20 | 20 | 20 |
| | 15 | 10 | 15 |
| Secale cereale | 20 | 15 | 15 |
| | 15 | 10 | 10 |
| | 10 | 5 | 10 |
| Triticum aestivum | 20 | 15 | 15 |
| Harmful plant: | | | |
| Capsella bursa-pastoris | 15 | 100 | 80 |
| Chenopodium album | 15 | 100 | 70 |
| Galium aparine | 15 | 100 | 75 |
| Lamium purpureum | 10 | 90 | 60 |
| Matricaria inodora | 5 | 100 | 65 |
| Thlaspi arvense | 5 | 100 | 70 |
| Polygonum convolvulus | 15 | 100 | 70 |
| Stellaria media | 5 | 100 | 50 |
| Viola arvensis | 5 | 90 | 40 |

TABLE 6

Comparison of the herbicidal activity of form II with form I, which is disclosed in WO 01/83459, when applied post-emergence (greenhouse)

| | | Active substance | |
|---|---|---|---|
| Test plants | Application rate (g/ha a.s.) | Form II | Form I |
| | | Damage [%] | |
| Useful plant: | | | |
| Hordeum vulgare | 20 | 0 | 5 |
| | 15 | 0 | 5 |
| Harmful plant: | | | |
| Kochia scoparia | 20 | 100 | 45 |
| Papaver rhoeas | 20 | 70 | 20 |
| Polygonum convolvulus | 20 | 100 | 40 |
| Salsola kali ssp. ruthenica | 20 | 100 | 80 |
| Sinapis arvensis | 10 | 80 | 50 |

TABLE 6-continued

Comparison of the herbicidal activity of form
II with form I, which is disclosed in WO 01/83459,
when applied post-emergence (greenhouse)

| Test plants | Application rate (g/ha a.s.) | Active substance | |
|---|---|---|---|
| | | Form II | Form I |
| | | Damage [%] | |
| *Thlaspi arvense* | 10 | 98 | 30 |
| *Veronica persicaria* | 15 | 80 | 40 |

The test results show clearly that form II according to the invention has a markedly improved herbicidal activity while exhibiting the same or better tolerance by the crop plant in comparison with form I, which is known.

We claim:

1. A crystalline, essentially solvent-free form II of 2-chloro-5-[3,6-dihydro-3-methyl-2,6-dioxo-4-(trifluoromethyl)-1-(2H)pyrimidinyl]-4-fluoro-N-[[methyl(1-methylethyl)amino]sulfonyl]benzamide, which in an X-ray powder diffractogram at 25° C. and Cu—K$_\alpha$ radiation, shows at least six of the following reflexes, given as 2θ values: 6.3±0.3°, 9.4±0.3°, 10.9±0.3°, 11.9±0.3°, 12.6+0.3°, 15.0±0.3°, 15.8±0.3°, 17.1±0.3°, 20.0±0.3°, 20.4±0.3°, 24.7±0.3°, 25.2±0.3°, 26.2±0.3°.

2. The crystalline form II according to claim 1 with a melting peak in the range of from 170 to 200° C. with a peak maximum in the range of from 180 to 190° C.

3. The crystalline form II according to claim 1 with a 2-chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl]benzamide content of at least 94% by weight.

4. A 2-Chloro-5-[3,6-dihydro-3-methyl-2,6-dioxo-4-(trifluoromethyl)-1-(2H)-pyrimidinyl]-4-fluoro-N-[[methyl-(1-methylethyl)amino]sulfonyl]benzamide, consisting essentially of the crystalline, essentially solvent-free form II which in an X-ray powder diffractogram at 25° C. and Cu—K$_\alpha$ radiation, shows at least six of the following reflexes, given as 2θ values: 6.3±0.3°, 9.4±0.3°, 10.9±0.3°, 11.9 1±0.3°, 12.6±0.3°, 15.0±0.3°, 15.8±0.3°, 17.1±0.3°, 20.0±0.3°, 20.4±0.3°, 24.7±0.3°, 25.2±0.3°, 26.2+0.3°.

5. A process for the preparation of the crystalline form II according to claim 1, comprising:

i) providing a solution of 2-chloro-5-[3,6-dihydro-3-methyl-2,6-dioxo-4-(trifluoromethyl)-1-(2H)-pyrimidinyl]-4-fluoro-N-[[methyl-(1-methylethyl)-amino]sulfonyl]benzamide in an organic solvent which is essentially free from water, ii) bringing about a crystallization of 2-chloro-5-[3,6-dihydro-3-methyl-2,6-dioxo-4-(trifluoromethyl)-1-(2H)-pyrimidinyl]-4-fluoro-N-[[methyl-(1-methyl-ethyl)amino]sulfonyl]benzamide over a period of at least 1 h.

6. The process according to claim 5, wherein the organic solvent is selected from the group consisting of $C_1$-$C_6$-alkanols, acyclic ketones having 3 to 8 carbon atoms, cyclic ketones having 5 to 8 carbon atoms, mono-$C_1$-$C_3$-alkylbenzenes, chlorobenzene, dichlorobenzenes, di-$C_1$-$C_6$-alkyl ethers, 5- or 6-membered alicyclic ethers, nitroalkanes having 1 to 3 carbon atoms, $C_1$-$C_4$-alkyl esters of aliphatic $C_1$-$C_4$-carboxylic acids, alkylnitriles having 2 to 6 carbon atoms, N,N-dimethylamides of aliphatic $C_1$-$C_4$-carboxylic acids, and their mixtures.

7. The process according to claim 5, wherein the crystallization is brought about by cooling and/or concentrating the solution provided in step i.

8. The process according to claim 5, wherein the crystallization is brought about by the addition of a solubility-reducing solvent.

9. The process according to claim 5, wherein the crystallization is effected in the presence of seed crystals of form II.

10. A plant protection composition comprising the crystalline form II according to claim 1 and auxiliaries conventionally employed for the formulation of plant protection compositions.

11. The plant protection composition according to claim 10, wherein the crystalline form II is suspended in the form of an aqueous suspension concentrate.

12. The plant protection composition according to claim 10, wherein the crystalline form II is suspended in the form of a nonaqueous suspension concentrate.

13. A method of controlling undesired vegetation, wherein the crystalline form II according to claim 1 is allowed to act on plants, their environment and/or on seeds.

14. The method of claim 13, wherein the crystalline form II has a melting peak in the range of from 170 to 200° C. with a peak maximum in the range of from 180 to 190° C.

* * * * *